US005718898A

United States Patent [19]
Broeker et al.

[11] Patent Number: 5,718,898
[45] Date of Patent: Feb. 17, 1998

[54] SACCHAROMYCES-SPECIFIC ANTIGENS AND ANTIBODIES, THEIR PREPARATION AND USE

[75] Inventors: Michael Broeker; Hans-Peter Harthus, both of Marburg, Germany

[73] Assignee: Behringwerke Aktiengesellschaft, Marburg, Germany

[21] Appl. No.: 377,737

[22] Filed: Jan. 25, 1995

[30] Foreign Application Priority Data

Jan. 25, 1994 [DE] Germany ............................ 44 02 065.1

[51] Int. Cl.$^6$ ............................................. A61K 39/395
[52] U.S. Cl. ................... 424/141.1; 424/184.1; 424/156.1; 424/152.1; 424/150.1; 530/388.1; 530/388.5
[58] Field of Search ................... 436/543; 435/7.31, 435/30, 7.32, 243, 252.33; 424/184.1, 141.1, 156.1, 152.1, 150.1; 530/388.1, 388.5

[56] References Cited

U.S. PATENT DOCUMENTS

| 5,156,968 | 10/1992 | Liu | 435/224 |
| 5,262,322 | 11/1993 | Liu et al. | 435/252.33 |
| 5,338,678 | 8/1994 | Senter et al. | 435/227 |

FOREIGN PATENT DOCUMENTS

A1 0 237 384  9/1987  European Pat. Off. .

OTHER PUBLICATIONS

Odds et al, Chapter 26, pp. 252–278, especially p. 274, 1988, Balliere Tindall, London, Candida and Candidoois, 2nd ed 1988.
Kononova, SV et al, FEMS Microbiology FEMS Microbiology Letters, vol. 113, pp. 77–80 1993.
Gil, ML et al, J. of Gen. Microbiol, vol. 137(5), pp. 1053–1061 1991.
J.P. Van Der Walt, "Saccharomyces Meyen Emend. Reess", Genus 16., pp. 55–718.
B.T. Heelan et al., "Identification of A 200–kDa Glycoprotein Antigen of Saccharomyces Cerevisiae", Immunology Letter, 28 (1991) p. 181–186.
J.A. Barnett, "The Taxonomy of the Genus Saccharomyces Meyen EX Reess:A Short Review of Non–Taxonomists", Yeast vol. 8:1–23 (1992).
G.I. Naumov et al., "Genetic Homology Between Saccharomyces Cerevisiae and Its Sibling Species S. Paradoxus & S. Bayanus: Electro. Karyotypes", Yeast vol. 8:599–612 (1992).
B.V. Kumar et al., "Cross–Reacting Human And Rabbit Antibodies To Antigens of Histoplasma Capsulatum, Candida Albicans...", Infection and Immunity, Jun. 1985, pp. 806–812.
L. Preller et al., "Potentially Allergenic Airborne Particles in the Vicinity of A Yeast and Penicillin Production Plant", JAPCA 39:1094–1097 (1989).

J.F. Kearney et al., "A New Mouse Myeloma Cell Line That Has Lost Immunoglobulin Expression But...", The Journal of Immunology, vol. 123, No.4 Oct. 1979, pp. 1548–1550.
Laemmli, "Cleavage of Structural Proteins During the Assembly of the Head of Bacteripophage T4", Nature vol. 227, Aug. 15, 1970, pp. 680–685.
Burnette, "Western Blotting" : Electrophoretic Transfer of Proteins From Sodium Bodecyl Sulfate–Polyacrylamide Gels... , Analytical Biochemistry 112, pp. 195–203 (1981).
Sakai et al., "Isolation and Characterization of Mutants Which Show an Oversecretion Phenotype in Saccharomyces Cerevisiae", Genetics 119: 499–506 (Jul. 1988).
Rudoph et al, "The Yeast Secretory Pathway is Perturbed by Mutations in PMR1. A Member of a $Ca^{2+}$Atpase Family", Cell, vol. 58, pp. 133–145, Jul. 14, 1989.
Heinemeyer et al., "Proteinase YSCE, The Yeast Proteasome/Multicatalytic–Multifunctional Proteinase: Mutants Unravel...", The EMBO Journal, vol. 10, No. 2 pp. 55–562, 1991.
Waltschewa et al., "Increased Extracellular Secretion in Fragile Mutants of Saccharomyces Cerevisiae", Seventh International Symposium on Yeasts, pp. 313–320, 1989.
Baldari et al., "A Novel Leader Peptide Which Allows Efficient Secretion of a Fragment of Human Interleukin...", The EMBO Journal, vol. 6, No. 1, pp. 229–234, 1987.
Price et al., "Expression, Purification and Characterization of Recombinant Murine Granulocyte–Macrophage Colony–Stimulating Factor...", Gene 55, pp. 287–293, (1987).
Bröker et al., Fems Microbiology Letters 118: 297–304 (1994).
Sandula et al., "Immunochemical studies on mannans of the genus Saccharomyces. Group of Saccharomyces sensu Strico Species,"Chemical Abstracts, 81: No. 19 (1974).
Sundstrom, PM et al, Infection & Immunity, Mar. 1988, p. 601–606, vol. 56(1).
Gairin, J.E. et al, FEMS Microbiol. Immunol., vol. 76, 1991, pp. 109–120.
Kononova, S.V et al, FEMS Micro Letters, 113, (1993) 77–80.
Harlow, E et al, "Antibodies A Laboratory Manual", 1988 Chapters 5 and 6.
Darroch, CJ et al, Immunology, 1994 V81, N2(Feb), pp. 247–252 (abstract).
Caetano, JA et al, Int. J. Immunopharmacol, 1986, 8(3) pp. 245–59 (abstract).

*Primary Examiner*—James C. Housel
*Assistant Examiner*—Ginny Allen Portner
*Attorney, Agent, or Firm*—Foley & Lardner

[57] ABSTRACT

Antibodies which are specific for *Saccharomyces cerevisiae, Saccharomyces bayanus, Saccharomyces paradoxus* and *Saccharomyces pastorianus*, and epitopes to which such antibodies bind are described. Diagnostic agents and assays for detecting *Saccharomyces sensu strictu* and epitopes of *Saccharomyces sensu strictu* also are described.

5 Claims, No Drawings

SACCHAROMYCES-SPECIFIC ANTIGENS AND ANTIBODIES, THEIR PREPARATION AND USE

FIELD OF THE INVENTION

The invention relates to antibodies which are specific for *Saccharomyces cerevisiae, Saccharomyces bayanus, Saccharomyces paradoxus* and *Saccharomyces pastorianus*, and to epitopes to which such antibodies bind. These antigens and antibodies can be employed for identifying and quantifying such Saccharomyces species.

BACKGROUND OF THE INVENTION

The identification and classification of the yeast genus Saccharomyces is of practical importance because some species are used in industries such as the beer, wine, baking and in biotechnology industries. Moreover, certain medical disorders are caused by yeast infections and appropriate treatment depends upon proper identification and classification of the species.

For example, excessive colonization of the intestine with yeasts can create large amounts of alcohol (gastrointestinal alcohol fermentation). This condition, called "alcohol autointoxication syndrome" or "autobrewery syndrome," can lead to painful disturbances in the health of patients. The ability to readily identify the causative agent of such a condition would be valuable.

Also, it is known that following infection with *S. cerevisiae*, immunosuppressed patients can contract a fungemia, a sometimes fatal disorder. Rapid and unambiguous identification of the involved yeasts could contribute to speedy therapy.

Further, the ability to differentiate various types of yeasts could be used to identify yeasts more rapidly in investigations of the type undertaken by Preller et al. *J. Air Waste Managm. Ass.* 39: 1094–1097 (1989). There, chronic, non-specific pulmonary disorders frequently appeared in the inhabitants of a town located near a yeast production plant and a penicillin production plant. In order to evaluate which yeasts were linked causally with this disease symptom, investigators determined the number of *S. cerevisiae* particles per cubic meter of air in region between the yeast production plant and the town. A rapid test would have permitted speedy identification of *S. cerevisiae*, and would have distinguished *S. cerevisiae* from other yeast species, such as, for example, Rhodotorula, which is frequently present in the air.

According to J. P. van der Walt, *Genus* 16: 555–718 (1970), 41 species are assigned to the genus Saccharomyces. However, many of these species have been assigned to other genera and renaming has taken place within the Saccharomyces genus. Currently, ten species are accepted within the Saccharomyces genus. See Barnett, J. A. *Yeast* 8: 1–23 (1992). These ten Saccharomyces species are: *S. bayanus, S. castellii, S. cerevisiae, S. dairensis, S. exiguus, S. kluyveri, S. paradoxus, S. pastorianus, S. servazzii*, and *S. unisporus*.

Moreover, in the future this classification likely will change because the rules and criteria by which taxonomic categorization of yeast species is undertaken are being changed. For example, one could argue that the species *S. bayanus, S. paradoxus* and *S. pastorianus* are not independent species but rather are varieties of *S. cerevisiae*.

Pursuant to Naumov et al. *Yeast* 8: 599–612 (1992), the following terminology is used for describing the present invention: *Saccharomyces cerevisiae, Saccharomyces bayanus, Saccharomyces paradoxus* and *Saccharomyces pastorianus* are combined as "*Saccharomyces sensu stricto*," in contrast to "*Saccharomyces sensu lato*", which is used to designate *Saccharomyces castellii, Saccharomyces dairensis, Saccharomyces exiguus, Saccharomyces kluyveri, Saccharomyces unisporus* and *Saccharomyces servazzii*. The yeast species are classified taxonomically first and foremost by morphological and physiological criteria (such as, for example, the utilization of carbon sources, dependence on growth factors, utilization of nitrogen sources, and the like) and also by mating behavior. DNA analysis also is used increasingly for determining relationships between yeast genera and yeast species.

On the other hand, immunological methods are only rarely employed for differentiating yeast species. One reason for this is that antibodies which are directed against cell wall-specific antigens cross-react to a large extent, both within a genus and beyond genera. The reason for the cross-reactivity within the genus Saccharomyces is that the cell wall-associated glycoproteins carry carbohydrate side groups which are made up of mannose chains that do not differ, or differ slightly, from species to species. There is also such a high degree of structural homology at the level of the polysaccharides (mannans and glucans) that any differentiation using antibodies would seem to be very difficult to achieve.

The difficulty in obtaining antibodies which are specific for a particular yeast species, in particular *S. cerevisiae*, is evident, for example, from Kumar et al. *Infection and Immunity* 1840 (1985), 806–812). The authors report that antibodies which were in each case prepared in rabbits against a representative of the species *Histoplasma capsulatum, Candida albicans* or *Saccharomyces cerevisiae* in each case also cross-react with the antigens of the other two species.

Consequently, a need exists for antibodies which react specifically with one or a few yeast species and thereby render it possible to use these antibodies to differentiate these yeast species from others. Such antibodies would be useful in certain foodstuff industries, such as the beer and wine industries, in the medical diagnostic industry and in the pharmaceutical industry for quality control purposes.

For example, monoclonal antibodies specific for *Saccharomyces sensu stricto* would be valuable in monitoring the culturing of *S. cerevisiae* (syn. *S. boulardii*) for use in drugs for treating diarrhea or for preparing recombinant proteins of *S. cerevisiae*. Such monoclonal antibodies also would be useful for diagnosing conditions such as "alcohol autointoxication syndrome," fungemia, and non-specific pulmonary disorders.

SUMMARY OF THE INVENTION

Thus, an object of the present invention is the preparation of antibodies or fragments thereof which specifically recognize the yeast species *Saccharomyces cerevisiae, Saccharomyces bayanus, Saccharomyces paradoxus* and *Saccharomyces pastorianus*, collectively referred to as *Saccharomyces sensu stricto*.

More specifically, the present invention relates to the monoclonal antibody Mab 92-276/018, or fragments thereof, from the hybridoma having the deposition number DSM ACC2126. Hereinafter this monoclonal antibody is referred to as "Mab DSM ACC2126" or "Mab 92-276/018."

The invention also relates to epitopes or immunogenic moieties from *Saccharomyces sensu stricto*, preferably from *Saccharomyces cerevisiae*, to which Mab 92-276/018 binds.

The invention further relates to antibodies or fragments thereof, which bind to epitopes or immunogenic moieties of *Saccharomyces sensu stricto*, preferably *Saccharomyces cerevisiae*, and which possess the same antigenic specificity as Mab 92-276/018.

In another embodiment, the invention relates to a hybridoma cell line that secretes Mab 92-276/018 or secretes a monoclonal antibody which possesses the same antigenic specificity of Mab 92-276/018.

In another embodiment the invention relates to a diagnostic agent for detecting *Saccharomyces sensu stricto* using the above described antibodies or fragments thereof and a detectable label.

The present invention additionally relates to a diagnostic agent for detecting antibodies against *Saccharomyces sensu stricto*, which diagnostic agent comprises (i) epitopes or immunogenic moieties from *Saccharomyces sensu stricto*, preferably *Saccharomyces cerevisiae*, to which the monoclonal antibody Mab 92- 276/018 binds and (ii) a detectable label.

The invention further relates to a process for preparing monoclonal antibodies involving the isolation of immunogenic moieties from *Saccharomyces sensu stricto*, preferably *Saccharomyces cerevisiae*, which react with the Mab 92-276/018; the immunization of a suitable host with these isolated antigens or immunogenic moieties; and the selection of the resulting monoclonal antibodies that are specific for *Saccharomyces sensu stricto*.

The present invention also relates to assays for identifying or quantifying *Saccharomyces sensu stricto* in a sample, wherein the sample is brought into contact with one of the above-described *Saccharomyces sensu stricto* specific antibodies and the resultant formation of antigen/antibody complexes is then measured using suitable methods.

The invention also relates to assays for detecting antibodies against *Saccharomyces sensu stricto* in a sample, wherein the sample is brought into contact with the above-described epitopes or immunogenic moieties from *Saccharomyces sensu stricto* and the formation of resultant antigen/antibody complexes is then measured using suitable methods.

In yet another embodiment, the invention relates to a kit for determining the presence of *Saccharomyces sensu stricto* in a sample comprising the above described monoclonal antibodies or fragments thereof.

DETAILED DESCRIPTION OF THE INVENTION

The present invention relates to antibodies, and fragments thereof, specific for *Saccharomyces sensu stricto*. Exemplary of a such an antibody within the present invention is monoclonal antibody 92-276/018 (DSM ACC2126). This antibody is directed against a cell wall-associated antigen gp-200. Mab 92-276/018 is specific for *Saccharomyces sensu stricto*, which includes *S. paradoxus, S. pastorianus, S. bayanus* and *S. cerivisiae*, as shown in the examples below.

The antibodies according to the present invention includes polyclonal and monoclonal antibodies. Monoclonal antibodies include any naturally or non-naturally occurring polypeptide having the binding specificity of Mab 92-276/018, that is, a polypeptide which binds to the same epitope on *Saccharomyces sensu stricto*, preferably *S. cerivisiae*, to which binds Mab 92- 276/018. Examples of such polypeptides include a half antibody molecule (a single heavy:light chain pair) or a fragment, such as the univalent fragments Fab or Fab' and the divalent fragment F(ab')2 ("FAB" meaning fragment antigen binding), that possess the same specificity for binding *Saccharomyces sensu stricto*, preferably *S. cerivisiae*, as Mab 92-276/018.

A fragment, according to the present invention may also be a single chain Fv fragment produced by methods well known in the art. See Skerra et al. *Science* 240: 1038–1041 (1988) and King et al. *Biochem. J.* 290: 723–729 (1991), each of which is incorporated by reference. The monoclonal antibodies of the present invention also include a non-peptide compound which is a "mimetic," i.e. a compound that mimics the epitope binding site of Mab 92-276/018 but that is water soluble, resistant to proteolysis and non-immunogenic. Conformationally restricted cyclic organic peptides which mimic Mab 92-276/018 can be produced in accordance with methods well known to the skilled artisan. See e.g., Sargovi, et al., *Science* 253:792–795 (1991), hereby incorporated by reference.

The terms "epitope" and "immunogenic moieties" as used in describing this invention, include any determinant responsible for the specific interaction with an antibody molecule. Epitopic determinants usually consist of chemically active surface groupings of molecules such as amino acids or sugar side chains and have specific three-dimensional structural characteristics, as well as specific charge characteristics.

The monoclonal antibodies of the present invention also include monoclonal antibody conjugates, which are for example, enzymes such as horseradish peroxidase, alkaline phosphatase and β-D-galactosidase and fluorescent markers, such as fluorescein, fluorochrome, rhodamine and the like. In such conjugates, the monoclonal antibody is bound to the enzyme or marker directly or by way of a spacer or linker group, such as ethylenediamine-tetraacetatic acid (EDTA) or the like.

Polyclonal and monoclonal antibodies can be produced in various ways using techniques well-understood by those having ordinary skill in the art. Details of these techniques are described in *Antibodies: A Laboratory Manual*, Harlow et al. Cold Spring Harbor Publications, p. 726 (1988), which is hereby incorporated by reference.

Generally, the monoclonal antibodies of the present invention are prepared by immunizing BALB/c mice subcutaneously and intraperitoneally with *S. cerivisiae* protein gp200, as described below in Examples 1 and 2. Spleens from the immunized mice are fused with SP2/0 myeloma cells and hybridomas secreting antibodies against gp200 are detected using an enzyme assay.

Thus, in one embodiment, the present invention relates to a hybridoma. This hybridoma secretes a monoclonal antibody that is specific for *Saccharomyces cerevisiae, Saccharomyces bayanus, Saccharomyces paradoxus* and *Saccharomyces pastorianus*. In particular, the hybridoma of the present invention secretes murine monoclonal antibody, Mab 92-276/018, which was deposited with the Deutsche Sammlung yon Mikroorganismen und Zellkulturen GmbH (DSM) (German Collection of Microorganisms and Cell Cultures), Mascheroder Weg 1 B, 38124 Braunschweig, on Apr. 22, 1993 under the number DSM ACC2126. The hybridoma cell lines of the present invention are genetically stable, secrete monoclonal antibodies of the invention and can be activated by standard techniques.

The monoclonal antibodies and fragments thereof according to this invention are multiplied according to in vitro and in vivo methods well-known in the art. Multiplication in vitro is carried out in suitable culture media such as Dulbecco's Modified Eagle Medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention also may be obtained by multiplying hybridoma cells in vivo. Cell clones are injected into mammals which are histocompatible with the parent cells, e.g. syngeneic mice, to cause growth of antibody producing tumors. Optionally, the animals are primed with hydrocarbon, especially oils such as pristaine (tetramethylpentadecane) prior to injection. After one to three weeks, the desired monoclonal antibody is recovered from the body fluid of the mammal.

In accordance with the present invention, fragments of the monoclonal antibody of the invention can be obtained form the monoclonal antibody produced as described above and in Example 2, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer as supplied by Applied Biosystems, Multiple Peptide Systems, etc. or they may be produced manually, using techniques well-known in the art. See Geysen, et al. *J. Immun. Methods* 102: 259–274 (1978), hereby incorporated by reference.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced.

Radioactively labeled monoclonal antibodies of the present invention are produced according to well-known methods in the art. For instance, monoclonal antibodies can be iodinated by contact with sodium or potassium iodide and a chemical oxidizing agent, such as lactoperoxidase. Monoclonal antibodies according to the invention may be labeled with technetium-99 m by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as SNC12, a buffer solution such as sodium-potassium phthalate solution, and the antibody. Radionuclides can be bound to an antibody either directly or indirectly by using an intermediary functional group. Intermediary functional groups which are often used to bind radioisotopes which exist as metallic ions to antibody are diethylene-triaminepentaacetic acid (DTPA) and ethylene diaminetetracetic acid (EDTA). Examples of metallic ions suitable for use in the invention are $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, $^{201}Tl$. In accordance with this invention, the monoclonal antibody or fragment thereof may be labeled by any of several techniques known to the art. See, e.g., Wagner et al. *J. Nucl. Med.* 20: 428 (1979) and Saha et al., *J. Nucl. Med.* 6: 542 (1976), hereby incorporated by reference.

Thus, in one embodiment, the invention relates to a diagnostic agent comprising the above describe monoclonal antibody and a label for the detection of *S. sensu stricto*. In another embodiment, the invention relates to a diagnostic agent for the detection of antibodies against *S. sensu stricto* comprising an epitope of *S. sensu stricto* and a detectable label.

The invention also relates to various immunological detection systems, such as Western blot, immunofluorescence test, enzyme-linked immunosorbent assay (ELISA), radioimmunoassay (RIA) and fluorescence immunoassay (FIA). Indeed, the invention includes in vitro assays for the detection of *S. stricto sensu* in whatever kind of sample it may occur, such samples including fluid, semi-fluid or tissue samples, using the monoclonal antibody or fragment thereof of the invention. The assay can be a competitive of sandwich assay, or any assay well-known to the artisan which depends on the formation of an antibody-antigen immune complex. For purposes of this invention, the monoclonal antibody or fragments thereof of the present invention can be immobilized or labeled. Many carriers are known to the skilled artisan to which the monoclonal antibody or fragments thereof of the present invention can be bound for immobilization. Where required, derivatization techniques can be used for immobilizing the monoclonal antibody or fragment thereof on a substrate. Well-known carriers include glass, polystyrene, polypropylene, polyethylene, dextran, nylon, amylases, natural and modified celluloses etc. The carrier can be either soluble or insoluble. Immunoassays encompassed by the present invention include, but are not limited to those described in U.S. Pat. Nos. 4,367,110 (double monoclonal antibody sandwich assay); Wide et al., Kirkham and Hunger, eds. *Radioimmunoassay Methods,* E. and S. Livingstone, Edinburgh (1970): U.S. Pat. No. 4,452,901 (Western Blot); Brown et al., *J. Biol. Chem.* 255: 4980–4983 (1980) (immunoprecipitation of labeled ligand); and Brooks et al. , *Clin. Exp. Immunol.* 39:477 (1980) (immunocytochemistry).

The in vitro assays of the present invention also include the use of epitopes or immunogenic moieties of *S. sensu stricto* in the detection of antibodies against *S. sensu stricto*. For example epitopes or immunogenic moieties may be bound to a solid substrate and used in assays to determine the effects of modifications to known monoclonal antibodies having the same binding affinity as Mab DSM ACC2126. Another assay involves the detection of monoclonal antibodies in samples which compete with Mab DSM ACC2126 in binding to *S. sensu stricto* or a polypeptide presenting the epitope of the invention. In that way, the presence of antibodies, for example from a patient sample (e.g., blood, urine, etc.), can be determined without the need for the epitope mapping discussed below.

From the disclosure provided herein, a skilled artisan readily could characterize, i.e., map, the epitope or immunogenic moieties of *S. sensu stricto* responsible for binding monoclonal antibodies having the same binding affinity as Mab DSM ACC2126. In this regard, see Example 8. Indeed, monoclonal antibody mapping analysis techniques are well-known in the art, see e.g. Regenmortal, *Immunology Today* 10: 266–72 (1989) and Berzofsky et al., *Immunological Reviews* 98: 9–52 (1987), and may include computer predictions of secondary structure and antigenicity to indicate the possible location of epitopes, particularly as conserved regions of the protein may be of structural or functional significance. Further investigations also involve crossblocking of monoclonal antibodies to define classes of monoclonal antibodies that bind to identical or overlapping regions. The predicted epitope is confirmed using cloned oligonucleotides or synthetic peptides. Important residues are then identified by mutagenesis or cloning of incorrect oligonucleotides or by using incorrect synthetic peptides. Alternatively, epitope mapping may be carried out according to the present invention by using homolog-scanning mutagenesis in conjunction with secondary structure analyses. See Cunningham, et al., Science 243: 1330–1336 (1989). This involves the synthesis of many small peptides that completely span the protein and allows identification of many small continuous epitopes of a protein or fragment. Another method of epitope mapping involves the random cloning of very small fragment of DNA encoding parts of the protein and screening each clone obtained with each available monoclonal antibody. See generally, Immunochemical Protocols, Manson, M. ed., vol. 10, Humana Press, Totowa, N.J. pp. 105–116 (1992).

Thus, in one embodiment, the appropriate sample of S. sensu stricto is digested into polypeptide fragments and binding assays using, for example, Mab DSM ACC2126, are performed to locate the polypeptide fragment responsible for binding the Mab. Subsequent sequencing of the fragment would provide the amino acid sequence of the epitope. See Manson, supra.

The polypeptide presenting the epitope then could be reproduced using standard cloning and expression techniques using procaryotic or eucaryotic hosts, depending upon the desirability of glycosylation of the epitope. For example, one could synthesize DNA encoding the amino acid sequence of the epitope, using preferred codons for the host. The length of the amino acid sequence used would depend upon the conformational requirements of the epitope, i.e., the length of sequence required to provide the conformation that yields acceptable binding to Mab DSM ACC2126. The DNA then could be inserted into a plasmid vector that in turn could be used to transfect the desired host. Upon culturing in appropriate growth medium, the epitope would be produced.

Skilled artisans readily may appreciate the many acceptable variations of the foregoing processes, as well as other ways in which the epitope could be characterized and reproduced by recombinant or non-recombinant means.

The monoclonal antibodies or fragments thereof of the present invention are suitable for use in a kit. Such a kit may comprise a receptacle being compartmentalized to receive one or more containers, such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention.

Without further elaboration, it is believed that one skilled in the art can, using the preceding description, utilize the present invention to its fullest extent. The following examples are merely illustrative and not limitative of the remainder of the disclosure in any way whatsoever.

EXAMPLE 1

Isolation of gp200

*S. cerevisiae gp*200 was isolated according to the method of Heelan et al. *Immuno. Lett.* 28: 181–186 (1991).

Specifically, *S. cerevisiae* was grown aerobically for 48 hours on Sabouraud agar (Oxoid) at 37° C. Soluble extracts (Sacc) were prepared as described previously in McKenzie et al. *Gut* 31: 536 (1990) and Barnes et al. *Int. Arch. Allergy Appl. Immuno.* 92: 9 (1990). Cells were harvested, washed twice in 0.15M saline, resuspended in saline (1:10, v/v) after centrifugation at 2000 xg for 10 minutes), the supernatant removed, sterile-filtered (0.2 μm) and stored in aliquots at −20° C. The protein concentration was determined by Bio-Rad protein assay.

Sera from CD patients containing IgG and IgA isotype-specific antiSacc antibodies were determined by enzyme-linked immunosorbent assay (ELISA) as previously described in Barnes, supra. Briefly, CD sera (1:100 dilution) were added to microtitre plates coated with Sacc (10 μ/ml), followed by peroxidase-conjugated rabbit anti-human γ or anti-α chain (1:1000). Sera with binding indices >3.0 were regarded as anti-Sacc antibody-positive. Barnes, supra. Control anti-Sacc antibody-negative sera were obtained from blood donors Barnes, supra.

Peroxidase-conjugated rabbit IgG anti-human Ig, anti-human gamma and anti-human alpha heavy chains, as well as peroxidase-conjugated swine (IgG anti-rabbit Ig, were obtained from Dako Ltd. (High Wycombe). Rabbit antiserum to *S. cerevisiae* was obtained by repeated immunization with soluble antigen (Sacc) in incomplete Freund's adjuvant: anti-Sacc antibody activity, compared with pre-immune serum, was determined by ELISA using peroxidase-conjugated swine anti-rabbit Ig.

Gels were run using the discontinuous buffer system of Laemmli, *Nature* 227: 680 (1970) with a 3% stacking gel and 12% resolving gel. Samples were reduced by heating at 100° C. for 2 minutes in 25 mM dithiothreitol (DTT; Sigma). 20-μl samples (1:1 in sample buffer) of whole *S. cerevisiae* (1:10, v/v in saline) solubilized in 2% SDS by heating at 100° C. for 2 minutes, or saline extract (i.e., Sacc) of *S. cerevisiae* (0.5 mg/ml), were applied to each gel. Gels were stained with Coomassie brilliant blue or periodic acid Schiff's reagent (PAS). Towbin et al. *Proc. Natl. Acad. Sci. USA* 76: 4350 (1979)

Transfer of antigens from gels on to nitrocellulose sheets (Gelman Sciences) was performed overnight in a Trans-Blot electrophoretic transfer cell (Bio-Rad). See Johnston et al. *Immunochem.* in Practice, Blackwell, Oxford (1987). After transfer, nitrocellulose strips were washed twice in Tris-buffered saline (TBS), pH 7.4, for 15 minutes, followed by a 30-minute wash in 10% foetal calf serum (FCS)/TBS. Strips were exposed to human sera containing anti-Sacc antibodies or antibody-negative control sera (diluted 1:100 in 10% FCS/TBS) for 2–3 hours. Unbound primary antibody was removed by two 15-minute washes in TBS, after which peroxidase-conjugated rabbit antihuman Ig, antiIgG or anti-IgA (diluted 1:500 in 10% FCS/TBS) was added for 1–2 hours. Following removal of unbound antibody with two 5-minute washes in distilled water, 0.1% 4-chloro-1-naphthol (Sigma) in TBS with fresh 0.02% $H_2O_2$ was used as substrate.

This was performed after transfer to nitrocellulose strips as described in Woodward et al., *J. Immunol. Methods* 78: 143 (1985). All strips were rinsed with 50 mM sodium acetate buffer, pH 4.5, after which control strips were incubated in the same buffer for 1 hour. Test strips were exposed to varying concentrations of sodium m-periodate, from 0.1 to 50 mM in pH 4.5 acetate buffer, for 1 hour in the dark at 23° C. Control and test strips were then rinsed with sodium acetate buffer, exposed to 50 mM sodium borohydride in phosphate-buffered saline, pH 7.4, for 30 minutes at 23° C., followed by a further 5 minute wash in TBS. Blotting was performed using rabbit anti-Sacc serum and pre-immune rabbit serum (NRS) (both 1:100 in 10/% FCS/TBS) followed, after washing, by peroxidase-conjugated swine anti-rabbit Ig (1:500).

SDS-PAGE of a saline extract (Sacc) of *S. cerevisiae* showed a single band of apparent size 200 kDa under reducing and non-reducing conditions. This band always stained with Coomassie blue, although weakly, and strongly with PAS. This 200 kDa glycoprotein migrated in identical position to a single glycoprotein band in SDS-solubilized whose *S. cerevisiae*.

Following SDS-PAGE of a saline extract of *S. cerevisiae* (Sacc) and SDS-solubilized *S. cerevisiae*, nitrocellulose strips were blotted with 8 anti-Sacc antibody-positive sera and two antibody-negative sera from CD patients. Eight out of 8 anti-Sacc antibody-positive sera reacted with a single band of apparent size 200 kDa present in both whole *S. cerevisiae* and Sacc. Confirmation of antibody-binding with the 200 kDa band in Sacc was obtained using eight sera containing IgG or IgA isotype-specific anti-Sacc antibodies. Reactivity with the 200 kDa band was obtained only with IgG and IgA specific anti-Sacc antibodies; control sera showed negative binding. Rabbit anti-Sacc serum showed identical reactivity with this 200 kDa band, compared with pre-immune rabbit serum which was non-reactive.

Confirmation of the glycoprotein composition of gp200 was obtained by periodate treatment of Sacc antigen, followed by blotting with the rabbit anti-Sacc serum. Increasing concentrations, up to 50 mM, of periodate caused increasing, but not complete, loss of immunoreactivity with the 200 kDa band.

EXAMPLE 2

Preparation of Monoclonal Antibodies against the Glycoprotein gp200 from *Saccharomyces cerevisiae*.

Balb/c mice which were six to eight weeks old were immunized with a glycoprotein (gp200), as described above. The gp200 can be isolated rapidly and simply by culturing *S. cerevisiae* (J. Sainsbury, PLC) overnight in YPD medium. The cells are harvested, washed twice in water and resuspended in 10 times the volume of water. The cell suspension is incubated for 1 hour in a water bath at 100° C. The cell preparation is then centrifuged for 5 minutes at 5000 rpm in a bench centrifuge (Varifuge 3.2 RS) and the supernatant concentrated approximately 3 times using a Centricon 100 k filtration system (tiltron).

Then, each mouse was injected subcutaneously with approximately 50 µg of the glycoprotein emulsified in complete Freund's adjuvant and, in a second instance, intraperitoneally. A second and a third immunization without adjuvant were in each case carried out four to eight weeks later. Immediately before the actual fusion, the experimental animals were additionally boosted intravenously on four days in succession. On the day of the fusion, the spleens were removed under sterile conditions and suspended to form individual cells. By means of fusing $10^8$ spleen cells with $2 \times 10^7$ cells of the myeloma cell line SP 2/0 or cell linex63 Ag 8653 (*J. Immunol.* 173: 1548–1550, [1979]), hybrid cells were produced which were subsequently sown in a selection medium (Dulbecco's minimal essential medium, DMEM, supplemented with 20% fetal calf serum FCS, 0.1 mM hypoxanthine, 0.4 mM aminopterin and 16 mM thymidine) on culture plates having 24 wells (from Costar) at a concentration of $10^6$ cells/well. Two to three weeks later, individual cell colonies were isolated from the wells and in each case transferred into a well of a new culture plate.

After a further two to three days, the culture supernatants were screened for the presence of gp200-specific antibodies using an enzyme immunoassay. The supernatants were incubated on gp200-coated microtitration plates and any specific antibodies which were present were detected by an anti-mouse peroxidase/immunoglobulin conjugate reaction. Positive cell lines were cultured up and, after testing for the absence of mycoplasmas, were frozen in liquid nitrogen. In parallel with this, positive cell lines were cloned using a micromanipulator. Suitable clones were then multiplied in cell culture (mass culture in roller bottles). Purification was carried out using ammonium sulfate precipitation and protein A chromatography. Purity was tested by means of HPLC and gel electro-phoresis and the immunoglobulin classes determined by Ouchterlony immunodiffusion.

EXAMPLE 3

Selection of Monoclonal Antibodies

Hybridoma supernatants are tested for their reactivity in Western blots using antigen from *Saccharomyces cerevisiae* and from *Schizosaccharomyces pombe* as a comparison.

For this purpose, *S. cerevisiae* (VLSF 07158) and *S. pombe* (CBS 1043) were cultured for 3 days, at 30° C. and at 180 rpm, in YPD medium (1% yeast extract, 2% peptone, 2% glucose) in 250 ml conical flasks on a shaking apparatus. After centrifuging 10 ml of culture both in each case, the cells were harvested, taken up in 1 ml of 10 mM Tris buffer (pH 7.5), provided with glass beads, and disrupted in a glass bead mill. Subsequently, the homogenate was heated in accordance with Laemmli, supra., fractionated in a 10% SDS polyacrylamide gel and transferred to nitrocellulose membranes (Burnette, *Anal. Biochem.*, 112: 195–203 [1981] ). The nitrocellulose strips were then incubated in Tris buffers (10 mM Tris HCl, pH 7.5, 150 mM NaCl, 1% gelatin, 4% tween 20) which in each case contained monoclonal antibodies, at a concentration 6 f approximately 10 µg/ml, from nine different hybridoma supernatants. Anti-mouse antibodies which were coupled to alkaline phosphatase were used as the conjugate. Fast Blue B salt (from Serva, Heidelberg) and Naphtol AS-MX Phosphate (from Sigma Chemie, Munich) were used as substrates. Rainbow® protein molecular weight markers (Amersham Buchler GmbH, Braunschweig) were additionally loaded onto the SDS polyacrylamide gel for determining the relative molecular mass.

All nine antibody specificities recognized antigens from *S. cerevisiae* in the Western blot.

Of nine supernatants tested, four were only very weakly positive:

-92-285/18
-92-285/27
-92-285/29
-92-275/02

Four supernatants exhibited quite good reactivity:

-92-285/5
-92-285/10
-92-285/15
-92-285/16

The strongest reactivity was shown by the supernatant -92-276/018.

By contrast, none of the nine supernatants recognized an antigen from S. pombe. This was judged to be the criterion for a specific immunoreactivity of the monoclonal antibodies.

In subsequent work, the reactivity of the monoclonal antibody 92-276/018 was investigated in more detail.

EXAMPLE 4

Specificity of Mab 92-276/018

The specificity of the monoclonal antibody 92-276/018 (DSM ACC2126) was analyzed in Western blots on the one hand and on intact yeast cells in immuno-fluorescence tests on the other.

Immunofluorescence on intact yeast cells using monoclonal antibodies was carried out as follows. The yeasts were cultured in media as described for the Western blot analyses. 10 µl of a yeast cell suspension were in each case introduced into the wells of immuno-fluorescence glass plates. After 1 hour of incubation at RT, the supernatant was sucked off and the cells were fixed by adding acetone cooled to 4° C. The plates were then rinsed with water and dried. 10 µl of the antibody solution (100 µg/ml) were pipetted into each well. After the plates had been incubated at 37° C. in a moist chamber for one hour, the supernatant was removed, the plates were washed three times, and FITC-labeled anti-mouse immunoglobulin conjugate was added.

Microscopic analysis was carried out after the plates had been incubated for one hour and then washed.

Mab 92-276/018 was examined with regard to its reactivity with different yeast species. The different yeast species were obtained from the following institutions: Deutsche Sammlung yon Mikroorganismen und Zellkulturen GmbH (DSM) (German Collection of Microorganisms and Cell Cultures), Braunschweig, Federal Republic of Germany; Centraalbureau voor Schimmelcultures (CBS) (Central Office for Mould Cultures), Baarn-Delft, Netherlands; Versuchs— und Lehranstalt für Spiritusfabrikation und Fermentationstechnologie in Berlin (VLSF) (Experimental and Educational Institute for Spirit Production and Fermentation Technology in Berlin), Berlin, Federal Republic of Germany; Institut für Mikrobiologie und Weinforschung (IMW) (Institute for Microbiology and Wine Research) of the Johannes Gutenberg University, Mainz, Federal Republic of Germany; Yeast Genetic Stock Center (YGSC), Berkeley, USA and J. Sainsbury PLC, London, England. In addition to this, some yeast strains were obtained from research institutes, which strains only have strain designations which are cited in the literature but do not conform to the nomenclature system of any official institute. The following yeast species were employed:

| Yarrowia lipolytica | DSM | 1345 |
|---|---|---|
| Debaromyces hansenii | DSM | 3428 |
| Hanseniaspora guilliermondii | DSM | 3432 |
| Schwanniomyces occidentalis | DSM | 3451 |
| Lipomyces starkeyi | DSM | 70295 |
| Pichia pastori | DSM | 70382 |
| Zygosaccharomyces bailii | DSM | 70492 |
| Saccharomycodes ludwigii | DSM | 3447 |
| Torulaspora delbrueckii | DSM | 70504 |
| Torulaspora pretoriensis | DSM | 70525 |
| Hanseniaspora uvarum | IMW | 473 |

-continued

| Schizosaccharomyces pombe | CBS | 1043 |
|---|---|---|
| Dekkera anomala | CBS | 4210 |
| Kluyveromyces marxianus | CBS | 369 |
| Pachysolen tannophilus | CBS | 4045 |
| Candida boidinii | CBS | 5777 |
| Candida albicans | CBS | 2730 |

In this collection of yeast species, four species are also represented which were previously assigned to the genus Saccharomyces:

| Kluyveromyces marxianus | ex Saccharomyces fragilis |
|---|---|
| | ex Saccharomyces lactis |
| Zygosaccharomyces bailii | ex Saccharomyces elegans |
| Torulaspora delbrueckii | ex Saccharomyces fermentati |
| Torulaspora pretoriensis | ex Saccharomyces pretoriensis |

These four yeast species, which at the time were assigned to the genus Saccharomyces on the basis of morphological and physiological criteria, and which exhibit a high degree of similarity with the genus Saccharomyces as regards taxonomic criteria, can thus be clearly delimited immuno-diagnostically from Saccharomyces cerevisiae using the monoclonal antibody 92-276/018.

None of these yeast species from different families reacted with the monoclonal antibody 92-276/018, either in the immunofluorescence test or in Western blot analyses.

EXAMPLE 5

Further reactivity of Mab 92-276/018 (wild)

Further work examined the reactivity of the monoclonal antibody 92-276/018 with different wild isolates of the species S. cerevisiae.

The following strains of S. cerevisiae were employed: S. cerevisiae DSM 70471 (ex. S. ellipsoideus) S. cerevisiae DSM 70478 (ex. S. chevallieri) S. cerevisiae DSM 70487 (ex. S. diastaticus) S. cerevisiae DSM 70514 (ex. S. italicus) S. cerevisiae CBS 5926 (ex. S. boulardii) S. cerevisiae IMW 116 S. cerevisiae IMW 188 S. cerevisiae IMW 25 S. cerevisiae IMW 92 S. cerevisiae VLSF 07158 S. cerevisiae J. Sainsbury, PLC S. cerevisiae YGSC X2180 1A All these strains reacted with the monoclonal antibody, both in the Western blot and in the immuno-fluorescence test. The first four strains examined had previously been assigned to different Saccharomyces species which are now no longer universally accepted, and all of them have been added to the species S. cerevisiae.

EXAMPLE 6

Further Reactivity of Mab 92-276/018 (lab)

Further work examined the reactivity of the monoclonal antibody with different laboratory strains of the species S. cerevisiae. The following table lists the strains examined, their genetic markers and their reactivity with the monoclonal antibody.

TABLE 1

Reactivity of the monoclonal antibody 92-276/018 with Saccharomyces cerevisiae laboratory strains

| Strain | Genetic Markers | Immunoblot | Immuno-fluorescence |
|---|---|---|---|
| C13ABYS86 | ura3–2,leu2,his,pra1,prb1, prc1,cps1 | + | + |
| HT 393 | ura3,leu2,pra1,prb1,prc1, cps1,pre1 | + | + |
| 79 | leu2,trp1 | + | + |
| S150-2B | leu2-3,leu2-112,ura3-52, tp1-289,his3Δ1 | + | + |
| TY 4 | leu2,ura3,ts1 | + | + |
| 4STLU | leu2,ura3,ts1,srb1 | + | + |
| CGY 1465 | leu2,ura3,ssc1/pmr1 | + | + |
| A 258 | can1,leu2,his4,met14,trp1, ura3,ose1,SUC2 | + | + |
| A 259 | can1,leu2,his4,met14,trp1, ura3,OSE1,SUC2 | + | + |

All the strains reacted, independently of the genetic markers. S. cerevisiae strains having an altered cell-wall structure or protein deletions in the periplasmic space due to genetic mutations, such as, for example, 4STLU, CGY 1465, TY 4 and A 258, were also recognized by the monoclonal antibody.

The laboratory strains of S. cerevisiae listed here are predominantly used for recombinant DNA purposes, and serve, in particular, as host cells for expressing heterologous proteins. These strains are freely available and are described in the literature with regard to their markers and possible uses. The specific references are:

A 258 and A 259: Sakai et al., Genetics 119, pp. 499–506 [1988].
CGY 1465: Rudolph et al., Cell 58, pp. 133–145 [1989].
C13ABYS86 and
HT 393: Heinemeyer et al, EMBO J. 10, pp. 535–562 [1991].
4STLU and TY 4: Waltschewa et al., Yeast 5, pp. 313–320 [1989].
S150-2B: Baldaft et al., EMBO J. 6, pp. 229–234 [1987].
79: Price et al., Gene 55, pp. 287–293 [1987].

EXAMPLE 7

Reactivity of 92-276/018 with Saccharomyces species other than S. cerevisiae

According to Barnett, ten species are nowadays assigned to the genus Saccharomyces. An investigation was next undertaken to determine whether the monoclonal antibody92-276/018 reacts with the other nine species in addition to S. cerevisiae.

The monoclonal antibody 92-276/018 showed no reaction in a Western blot and in an immunofluorescence test with the following Saccharomyces species:

| S. exigus | CBS 134 |
|---|---|
| S. dairensis | CBS 421 |
| S. unisporus | CBS 398 |
| S. servazzii | CBS 4311 |
| S. castelli | CBS 4309 |
| S. kluyveri | CBS 2861 |

However, the monoclonal antibody recognized the species:

| S. bayanus | DSM 70412 |
|---|---|
| S. bayanus | DSM 70511 |
| S. bayanus | DSM 70547 |
| S. pastorianus | DSM 6580 |
| S. pastorianus | CBS 1260 |
| S. paradoxus | CBS 406 |
| S. paradoxus | CBS 2980 |
| S. paradoxus | CBS 432 |

It is evident, therefore, that antibodies against the gp200 from S. cerevisiae and, in particular, the monoclonal antibody 92-276/018, represent suitable agents for identifying the species S. cerevisiae or, alternatively, characterizing a yeast species other than S. cerevisiae to show that this species cannot possibly be S. cerevisiae.

The fact that the monoclonal antibody 92-276/018 recognizes the species S. paradoxus, S. pastorianus and S. bayanus in addition to S. cerevisiae does not indicate lack of specificity. Extensive DNA studies have revealed that S. paradoxus and S. bayanus exhibit an exceptionally high degree of relatedness with S. cerevisiae (Naumov et al., Yeast, 8: 599–612 [1992]). In addition to this, the species S. pastorianus is considered to be a hybrid of the species S. cerevisiae and S. bayanus. This high degree of similarity between the species led Naumov et al. to describe these Saccharomyces species as being sibling species of S. cerevisiae.

Because the underlying criteria for determining yeast species are subject to variation and alteration with time, the species S. paradoxus, S. pastorjanus and S. bayanus should not be regarded as independent species but rather as varieties of S. cerevisiae. However, even if Barnett's classification of the species within the genus Saccharomyces is accepted as being valid, the monoclonal antibodies of the present invention are of great value because they identify a yeast isolate as belonging to the genus Saccharomyces and exclude several species within this genus.

EXAMPLE 8

Analysis of Epitope

Applicants observed that if nitrocellulose paper onto which proteins of S. cerevisiae cell extracts have been transferred from polyacrylamide gels is incubated in periodate solutions and the reactivity which remains is subsequently investigated using the monoclonal antibody 92-276/018, after a 30-minute incubation in the presence of 0.1 mM periodate, the full reactivity is still present. By contrast, applicants detected no binding of the monoclonal antibody 92-276/018 when the nitrocellulose strips were incubated in 10 mM or 50 mM periodate.

The reactivity is strongly affected when the incubation of the monoclonal antibody with the nitrocellulose coated with S. cerevisiae antigens is carried out in the presence of 100 mM methyl-α-D-methylmannoside. By contrast, the reactivity is undiminished as compared with the control, to which no sugars have been added, in the presence of methyl-α-D-methylglucanoside.

Applicants conclude from these two findings that the antigenic determinants which are recognized by the monoclonal antibody 92-276/018 probably represent carbohydrate structures, or represent peptide structures whose affinity for the antibody is influenced by carbohydrate sidechains.

In Western blot analyses, it is not only antigen which bands in SDS gels with an apparent molecular weight of 200 kDa which is recognized by the monoclonal antibody 92-276/018 (Mab DSM ACC2126); rather, the specific reactivity extends over a relatively wide range from about 40 kDa to 200 kDa. This indicates that mannoproteins or mannans are being recognized which are very heterogeneous in their molecular weight. It is probable that the monoclonal antibody recognizes a carbohydrate-specific epitope which can be a constituent of several glycoproteins or mannan structures and that gp200 represents only one antigen of several in *S. cerevisiae* having such an epitope.

What is claimed is:

1. A monoclonal antibody or fragment thereof which specifically binds to gp200 of *Saccharomyces sensu stricto* but does not cross-react with any other species of yeast.

2. The antibody or fragment thereof of claim 1, which is monoclonal antibody 92-276/018 (DSM ACC2126) or fragment thereof.

3. A hybridoma cell line that secretes the antibody of claim 1.

4. The hybridoma of claim 3 which secretes monoclonal antibody 92-276/018.

5. A process for preparing monoclonal antibody which specifically binds to gp200 of *Saccharomyces sensu stricto* but does not cross-react with any other species of yeast, the method comprising:

(a) isolating an epitope from *Saccharomyces sensu stricto* using monoclonal antibody 92-276/018;

(b) immunizing a suitable organism with said epitope so as to produce monoclonal antibodies; and (c) selecting the monoclonal antibodies produced in step (b) that are specific for *Saccharomyces sensu stricto*.

* * * * *